United States Patent [19]

Kitagawa et al.

[11] Patent Number: 5,652,335

[45] Date of Patent: Jul. 29, 1997

[54] PHYSIOLOGICALLY ACTIVE SUBSTANCE WELL CAPABLE OF PERMEATING BIOMEMBRANE

[75] Inventors: Kouki Kitagawa, Tokushima; Toru Hibi, Kawasaki; Noriko Tsuzuki, Kagawa, all of Japan

[73] Assignee: Teikoku Seiyaku Kabushiki Kaisha, Kagawa, Japan

[21] Appl. No.: 227,997

[22] Filed: Apr. 15, 1994

Related U.S. Application Data

[63] Continuation of Ser. No. 920,582, filed as PCT/JP91/00256, Feb. 27, 1991, abandoned.

[30] Foreign Application Priority Data

Feb. 28, 1990 [JP] Japan ......................... 2-50116

[51] Int. Cl.$^6$ .................. A61K 38/00; C07K 5/00; C07K 7/00; C07H 19/00
[52] U.S. Cl. ................. 530/330; 530/302; 530/402; 536/22.1; 536/28.4; 536/17.2; 536/18.7; 514/43; 514/49; 514/50; 548/543
[58] Field of Search ................. 530/330, 302, 530/402; 548/543; 536/22, 23, 17.2, 18.7; 514/43, 49, 50

[56] References Cited

U.S. PATENT DOCUMENTS

| | | | |
|---|---|---|---|
| 4,128,639 | 12/1978 | Lin et al. | |
| 4,273,704 | 6/1981 | Mazur et al. | 530/302 |
| 4,661,512 | 4/1987 | Laruelle et al. | 514/423 |
| 4,851,519 | 7/1989 | Lambert et al. | 536/23 |

FOREIGN PATENT DOCUMENTS

| | | |
|---|---|---|
| 0 187 052 | 10/1985 | European Pat. Off. |
| 0 257 378 | 8/1987 | European Pat. Off. |
| 2 352 618 | 8/1974 | Germany |
| 51-43769 | 4/1976 | Japan |
| 55-149299 | 11/1980 | Japan |
| 63-295590 | 12/1988 | Japan |

OTHER PUBLICATIONS

Tomatis, et al; *Amide, 1-Adamantylamide of Leu-Enkephalin and Leu-[D ALA$^2$]Enkephalin;* Ed. Scient., vol. 34, pp. 496–506, Il Farmaco, 1978.

Database WPI, Week 8104, 1981, Derwent Publications Ltd., London, GB; AN 81-04915D.

*Primary Examiner*—Jill Warden
*Assistant Examiner*—A. M. Davenport
*Attorney, Agent, or Firm*—Oblon, Spivak, McClelland, Maier & Neustadt, P.C.

[57] ABSTRACT

A physiologically active substance well capable of permeating biomembrane according to the present invention is represented by:

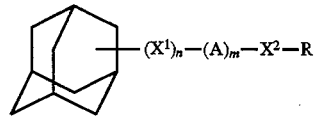

where R represents a residue of a physiologically active substance comprising a peptide, amino acid, aliphatic amine having a phenol skeleton, amino sugar, nucleoside or lactam compound and a residue of physiologically active derivative thereof. The biomembrane permeability of a substance with poor biomembrane permeability can be improved by introducing an adamantyl group to the physiologically active substance.

18 Claims, 5 Drawing Sheets

```
Proto type  H-Tyr-D.Ala-Gly-Phe-Leu-OH a       H-Tyr-D.Ala-Gly-Phe-Leu-O-Ada b       H-Tyr-D.Ala-Gly-Phe-Leu-NH-Ada c       H-Tyr-D.Ala-Gly-Phe-Leu-O-CH₂-Ada d       H-Tyr-D.Ala-Gly-Phe-Leu-O-CH₂-CH₂-Ada
```

-Ada=1-adamantyl

Proto type   H-Tyr-D.Ala-Gly-Phe-Leu-OH a   H-Tyr-D.Ala-Gly-Phe-Leu-O-Ada b   H-Tyr-D.Ala-Gly-Phe-Leu-NH-Ada c   H-Tyr-D.Ala-Gly-Phe-Leu-O-CH$_2$-Ada d   H-Tyr-D.Ala-Gly-Phe-Leu-O-CH$_2$-CH$_2$-Ada -Ada=1-adamantyl

PHYSIOLOGICALLY ACTIVE SUBSTANCE WELL CAPABLE OF PERMEATING BIOMEMBRANE

This application is a continuation of application Ser. No. 07/920,582, filed Aug. 28, 1992, abandoned, which was filed as International Application No. PCT/JP91/00256 on Feb. 27, 1991.

TECHNICAL FIELD

The present invention concerns a physiologically active substance having high biomembrane permeability, more specifically, blood-brain barrier (BBB) permeability. Since the physiologically active substance according to the present invention has a high blood-brain barrier permeability, it can provide a sufficient intraventricular physiological activity even by means of subcutaneous administration or intravenous injection which is simpler than intraventricular administration.

BACKGROUND ART

Morphine as an opioid alkaloid in a poppy has been known from long since to have an effective analgesic effect and has been utilized with an aim of mitigating a keen pain typified in the terminal stage of cancer. However, since morphine has side-effects such as addiction, dependence, depression of respiration and constipation, it has drawbacks that its use is rather restricted and the way of use is difficult. In view of the above, it has been strongly demanded for the development of an analgesic having an analgesic effect equal or superior to morphine and showing no addiction such as morphine.

On the other hand, enkephalin which is an endogenic morphine-like substance (endogenic opioid) was found by J. Hughes et. al, in 1975 and it has been expected as a substance capable of substituting for morphine. However, it has been found that enkephalin and derivatives thereof involve drawbacks in that (1) they are peptides and, accordingly, decomposed rapidly by enzymes in a living body, (2) they are poor in the BBB permeability and have to be administrated directly into a brain, and (3) they show similar side-effects to those of morphine such as addiction or dependence although they are endogenic substance.

For overcoming the foregoing drawbacks of the enkephalins, various studies have been made also at present but most of them have been directed to the enhancement of analgesic activity and moderation of the side-effects of the enkephalins in the vitro test or intraventricular administration test, as well as development for derivatives having high resistivity to decomposition by in vivo enzymes. In view of the foregoing situations, the present inventors have tried an improvement for the BBB permeability, which has not yet been studied by so much. Further, it has been expected that if the BBB permeability of the enkephalins can be improved, the BBB permeability of other substances with poor BBB permeability can also be increased to extend the application region.

DISCLOSURE OF THE INVENTION

The physiologically active substance well capable of permeating biomembrane according to the present invention has a feature in that it is represented by the general formula:

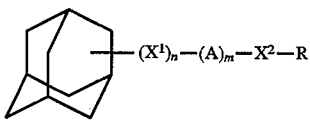

where $X^1$ and $X^2$, which may be identical or different with each other, represent an ether bond, urethane bond, ester bond or amide bond, A represents a lower alkylene group in which n=0 if m=0 and n=0 or 1 if m=1. Further, R is a residue of a physiologically active substance comprising a peptide, amino acid, aliphatic amine having a phenol skeleton, amine, amino sugar, nucleoside or lactam compound as well as a residue of a physiologically active derivative thereof.

As has been described above, adamantyl groups are introduced to the physiologically active substance according to the present invention, so that the poor BBB permeability of the physiologically active substance can be improved. Accordingly, it has been shown such a possibility as capable of administrating, by way of hypodermic injection, kephalins and such that have not hitherto shown analgesic effect unless directly administrated intraventricularly.

As the physiologically active substance used in the present invention, there can be mentioned, for example, peptides such as enkephalin, thyrotropine releasing hormone, adrenocorticotropic hormone, cholecystokinin, P-substance and GRF, amino acid such as methotrexate or leukoborine, aliphatic amine having a phenol skeleton such as norepinephrine or dopamin, amino sugar such as daunorubicin, adriamycin, doxorubicin, nucleoside such as zidovudine and lactam compound such as 2-pyrrolidone.

In the present invention, one or more of optional positions in the adamantyl group may be substituted with a group for enhancing the BBB permeability of the physiologically active substance. As the specific group, there can be mentioned, for example, lower alkyl group such as methyl group or ethyl group, hydroxyl group, lower alkoxy group, amino group, carboxyl group and carboxy lower alkyl group. It is, however, desirable that the compound is not so much hydrophilic.

According to the present invention, the BBB permeability can be enhanced by introducing the adamantyl group to a substance of poor BBB permeability to provide a possibility that enkephalins and such showing no analgesic effect unless directly administrated intraventricularly.

BRIEF DESCRIPTION OF THE DRAWINGS

FIG. 2 is a graph illustrating the result of measurement for the in vivo analgesic activity of the derivative a;

BEST MODE FOR PRACTICING THE INVENTION

The present inventors have made various studies for improving the BBB permeability of the enkephalin derivative and, as a step therefor, have tried to introduce an adamantyl group for improving the fat solubility.

As a proto type before introducing the adamantyl group, a derivative: H-Tyr-D.Ala-Gly-Phe-Leu-OH in which the second Gly from the N-terminus of enkephalin is substituted with D-Ala was used. For the above-mentioned derivative, it has already been reported that the derivative has a high resistivity to an aminopeptidase and has enhanced analgesic effect.

The following four kinds of derivatives in which the adamantyl group is introduced to the derivative were synthesized, in which Ada represents an adamantane residue.

H-Tyr-D.Ala-Gly-Phe-Leu-O-Ada                (A)

At first, Z-Tyr(Bzl)-D-Ala-Gly-NHNH$_2$ and H-Phe-Leu-O-Ada were synthesized, both of them were condensated by an azide method to obtain a pentapeptide protected at the N-terminus, which was then decapped by catalytic reduction to obtain a derivative a.

H-Tyr-D.Ala-Gly-Phe-Leu-NH-Ada               (B)

The derivative b was obtained by using H-Phe-Leu-NH-Ada instead of H-Phe-Leu-O-Ada and applying the same treatment as In (A) described above.

H-Tyr-D.Ala-Gly-Phe-Leu-O-CH$_2$-Ada         (C)

H-Tyr-D.Ala-Gly-Phe-Leu-O-(CH$_2$)$_2$-Ada   (D)

Figure 1:
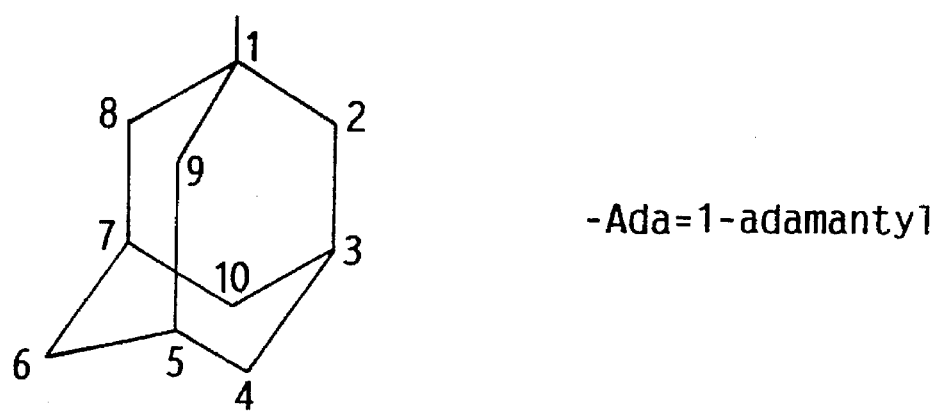
FIG. 1 is a view illustrating the structural formula of an enkephalin derivative (proto type a–d)

The derivatives c and d are obtained by applying the same treatment as in (A) above by using H-Phe-Leu-O-CH$_2$-Ada or H-Phe-Leu-O-(CH$_2$)$_2$-Ada (refer to FIG. 1).

Descriptions will be made more in details to each of synthesizing steps. In the present specification, abbreviations for amino acid residues and respective protection groups used herein are the followings in accordance with the customary practice in the relevant field.

Tyr: L-tyrosine
Gly: glycine
Phe: L-phenylalanine
Leu: L-leucine
GABA: γ-amino butyric acid
D.Ala: D-alanine
Z: benzyloxycarbonyl
Z(OMe): p-methoxybenzyloxycarbonyl
Ada: 1-adamantyl
Bzl: benzyl
ONp: p-nitrophenyl ester
OSu: N-hydroxy succinic imide ester
OMe: methyl ester
OAda: 1-adamantyloxy
NHAda: 1-adamantyl amino
NHNH$_2$: hydrazide
DCC: dicyclohexyl carbodiimide
DBU: 1,8-diazabicyclo[5,4,0]-7-undecene
TFA: trifluoro acetic acid
THF: tetrahydrofuran
DMA: N,N-dimethylacetamide
DMAP: 4,4-dimethylaminopyridine
DMF: dimethylformamide Further, in the thin layer chromatography (TLC), silica gel is used and the solvent system is as shown below:

Rf$_1$=CHCl$_3$: MeOH: H$_2$O (8:3:1)
Rf$_2$=CHCl$_3$: MeOH (10:1)
Rf$_3$=CHCl$_3$: MeOH (20:1)
Rf$_4$=CHCl$_3$: MeOH (50:1)
Rf$_5$=CHCl$_3$

Example 1

Preparation of H-Try-D.Ala-Gly-Phe-Leu-OAda (1) Preparation of Z-Leu-OAda

Z-Leu-OH (3.00 g, 11.3 mmol) was dissolved in methylene chloride (30 ml), to which adamantan-1-ol (1.9 g, 12.4 mmol), DCC (2.60 g, 12.4 mmol) and DMAP (0.15 g, 1.24 mmol) were added and stirred at 4° C. for 72 hours. After removing the resultant urea derivative by filtration, the solvent was distilled off. The residue was dissolved in ethyl acetate, and the ethyl acetate layer was washed with an aqueous 5% solution of sodium carbonate, an aqueous 10% solution of citric acid, an aqueous saturated solution of sodium chloride and then water successively. After drying with sodium sulfate, ethyl acetate was distilled off. Further, the residue was dissolved in chloroform and then purified with silica gel column chromatography. From the chloroform elution fraction, an oily product showing a single spot was obtained.

Yield: 3.10 g (69%)

(2) Preparation of Z-Phe-Leu-OAda

Z-Leu-OAda (6.20 g, 15.5 mmol) was dissolved in THF (30 ml), to which two drops of acetic acid and 5% palladium-carbon (2.0 g) were added and a hydrogen gas was passed therethrough for 2 hours. After removing palladium-carbon by filtration, the filtrate was condensated and the residue was dissolved in DMF (70 ml). Triethylamine (2.14 ml, 15.5 mmol) and Z-Phe-ONp (4.64 g, 15.5 mmol) were added to the solution and stirred for 48 hours. After removing DMF by distillation, the residue was dissolved in ethyl acetate and washed with an aqueous 10% solution of citric acid, an aqueous 5% solution of sodium carbonate, an aqueous saturated solution of sodium chloride and water successively. After drying with sodium sulfate, ethyl acetate was distilled off. Further, the residue was dissolved in chloroform, and an oily product showing a single spot was obtained by silica gel column chromatography using chloroform as an eluting solution.

Yield: 4.25 g (51%)

(3) Preparation of Z(OMe)-D.Ala-Gly-OMe

Z(OMe)-D.Ala-OH (5.06 g, 20 mmol) was dissolved in DMF and a mixed acid anhydride was prepared from triethylamine (3.04 ml, 22 mmol) and isobutylchloroformate (2.88 ml, 22 mmol). H-Gly-OMe hydrogen chloride (2.07 g, 16.5 mmol) was dissolved in DMF (20 ml) and neutralized with triethylamine (2.30 ml, 16.5 mmol). Both of the solutions were mixed and stirred under ice cooling for 2 hours. After distilling off DMF, the residue was dissolved in ethyl acetate and washed with an aqueous 10% solution of citric acid, an aqueous 5% solution of sodium carbonate, an aqueous saturated solution of sodium chloride and then with water successively. After drying with sodium sulfate, ethyl acetate was distilled off and ether was added to the residue to obtain powder. After collecting the powder by filtration, it was recrystallized from ethyl acetate - ether.

Yield: 3.10 g (58%), Melting point: 99°–101° C.

Rf$_1$: 0.75

Elemental analysis $C_{15}H_{20}N_2O_6$ Calculated value: C 55.55, H 6.22, N 8.64 Measured value: C 55.41, H 6.34, N 8.68

(4) Preparation of Z-Tyr(Bzl)-D.Ala-Gly-OMe

TFA (6.0 ml) - anisole (1.5 ml) were added to Z(OMe)-D.Ala-Gly-OMe (3.00 g, 9.25 mmol) under ice cooling and stirred for one hour. After distilling off TFA, the residue was dissolved in DMF (30 ml) and neutralized with triethylamine (1.28 ml, 9.25 mmol). Z-Tyr(Bzl)-OH (3.81 g, 11.1 mmol) was dissolved in DMF (40 ml) to which a mixed acid anhydride prepared from N-methylmorpholine (1.34 ml, 12.2 mmol) and isobutylchloroformate (1.60 ml, 12.1 mmol) were added and stirred under ice cooling for 2 hours. After distilling off DMF, the residue was dissolved in ethyl acetate, and washed with an aqueous 10% solution of citric acid, an aqueous 5% solution of sodium carbonate, an aqueous saturated solution of sodium chloride and water successively. After drying with sodium sulfate, ethyl acetate was distilled off and isopropyl ether was added to the residue to obtain powder. After collecting it by filtration, it was recrystallized from methanol - ether.

Yield: 3.31 g (65%), Melting point: 157°–161° C.
$Rf_1$: 0.81
Elemental analysis $C_{30}H_{33}N_3O_7$ Calculated value: C 65.80, H 6.07, N 7.67 Measured value: C 65.33, H 6.06, N 7.60

(5) Preparation of Z-Try(Bzl)-D.Ala-Gly-NHNH$_2$

Z-Tyr(Bzl)-D.Ala-Gly-OMe (3.20 g, 5.8 mmol) was dissolved in DMF (40 ml), to which 80% hydrazine hydrate (3.60 ml, 1.58 mml) was added and stirred for 24 hours. After distilling off DMF, ethanol was added to the residue to obtain powder. After collecting it by filtration, it was recrystallized from DMF - ethanol.

Yield: 3.15 g (98%), Melting point: 171°–174° C.
$Rf_1$: 0.61
Elemental analysis $C_{29}H_{33}N_5O_6 \cdot H_2O$ Calculated value: C 61.58, H 6.24, N 12.38 Measured value: C 61.73, H 6.06, N 12.86

(6) Preparation of Z-Tyr(Bzl)-D.Ala-Gly-Phe-Leu-OAda

Z-Phe-Leu-OAda (1.00 g, 1.83 mmol) was dissolved in tetrahydrofuran (20 ml), to which 5% palladium-carbon (about 1 g) was added and catalytic reduction was applied by passing a hydrogen gas. 2 hours after, the catalyst was removed by filtration, the solvent was distilled off and the residue was dissolved in DMF (50 ml). An azide ingredient prepared from Z-Tyr(Bzl)-D.Ala-Gly-NHNH$_2$) (1.30 g, 2.38 mmol) and triethylamine (0.70 ml, 5.0 mmol) were added and stirred at 4° C. for 24 hours. After distilling off DMF, water is added to the residue to obtain powder. The power was collected by filtration and then washed with an aqueous 10% solution of citric acid, an aqueous 5% solution of sodium hydrogen carbonate, an aqueous saturated solution of sodium chloride and water successively. After drying, it was recrystallized twice from methanol - ether.

Yield: 1.67 g (85%), Melting point: 136°–139° C.
$Rf_1$: 0.38
Elemental analysis $C_{54}H_{65}N_5O_9 \cdot \frac{1}{2}H_2O$ Calculated value: C 69.21, H 7.17, N 7.47 Measured value: C 69.29, H 7.23, N 7.33

(7) Preparation of H-Tyr-D.Ala-Gly-Phe-Leu-OAda

Z-Tyr(Bzl)-D.Ala-Gly-Phe-Leu-OAda (250 mg, 0.27 mmol) was dissolved in THF (30 ml), to which 5% palladium-carbon (1 g) was added and catalytic reduction was applied for 5 hours. After removing the catalyst by filtration, the solvent was distilled off and the residue was dissolved in a small amount of chloroform - methanol (10:1). A single fraction was obtained by silica gel column chromatography using the same solvent as the eluting solution, the solvent was distilled off and ether was added to the residue to obtain powder.

Yield: 85 mg (85%), Melting point: 110°–115° C.
$Rf_1$: 0.53, $[\alpha]_D = +159.6°$ (C=0.2, DMF, 25° C.)
Elemental analysis $C_{39}H_{53}N_5O_7 \cdot 2H_2O$ Calculated value: C 63.31, H 7.77, N 9.47 Measured value: C 63.56, H 7.66, N 9.05
FAB-MS: 704.0 [M+H]$^+$
Amino acid analysis value after hydrolysis with 6N hydrogen chloride
Gly 1.13, Ala 1.03, Leu 1.00, Tyr 0.88, Phe 1.05

Example 2

Preparation of H-Tyr-D.Ala-Gly-Phe-Leu-NHAda (1) Preparation of Z-Leu-NHAda

Z-Leu-OH (1.75 g, 6.6 mmol) was dissolved in DMF (30 ml), to which triethylamine (0.94 ml, 6.8 mmol) and isobutylchloroformate (0.90 ml, 6.8 mmol) were added to prepare a mixed acid anhydride. A solution prepared by dissolving 1-aminoadamantane hydrogen chloride (1.88 g, 10 mmol) in DMF (20 ml) and neutralizing with triethylamine (1.38 ml, 10 mmol) was added to the above-mentioned solution and stirred under ice cooling for 2 hours. After distilling off the solvent, the residue was dissolved in ethyl acetate and washed with an aqueous 10% solution of citric aid, an aqueous 5% solution of sodium carbonate, an aqueous unsaturated solution of sodium chloride and water successively. After drying with sodium sulfate, ethyl acetate was distilled off and petroleum ether was added to the residue to obtain powder. After collecting it by filtration, it was recrystallized from ethyl acetate - petroleum ether.

Yield: 2.20 g (84%), Melting point: 103°–105° C.
$Rf_5$: 0.44
Elemental analysis $C_{24}H_{34}N_2O_3$ Calculated value: C 72.33, H 8.60, N 7.03 Measured value: C 72.02, H 8.78, N 6.82

(2) Preparation of Z-Phe-Leu-NHAda

Z-Leu-NHAda (2.20 g, 5.5 mmol) was dissolved in methanol (30 ml), to which two drops of acetic acid and 5% palladium-carbon (about 1 g) were added and catalytic reduction was applied for 2 hours. After removing the catalyst by filtration, the filtrate was concentrated and the residue was dissolved in DMF (20 ml). The solution after the catalytic reduction was added to a DMF solution (20 ml) of a mixed acid anhydride prepared from Z-Phe-OH (1.98 g, 6.63 mmol), triethylamine (1.00 g, 7.29 mmol) and isobutylchloroformate (0.96 ml, 7.29 mmol) and they were stirred under ice cooling for two hours. After distilling off DMF, water was added to the residue to form powder, which was collected by filtration. It was washed with an aqueous 10% solution of citric acid, an aqueous 5% solution of sodium carbonate, an aqueous saturated solution of sodium chloride and water successively. After drying, it was recrystallized from ethyl acetate - petroleum ether.

Yield: 2.20 g (68%), Melting point: 125°–127° C.
$Rf_4$: 0.58
Elemental analysis $C_{33}H_{43}N_3O_4 \cdot \frac{1}{2}H_2O$ Calculated value: C 71.45, H 8.00, N 7.58 Measured value: C 71.57, H 8.08, N 7.61

(3) Preparation of Z-Tyr(Bzl)-D.Ala-Gly-Phe-Leu-NHAda

Z-Phe-Leu-NHAda (1.00 g, 1.83 mmol) was dissolved in THF (20 ml), to which two drops of acetic acid and 5% palladium-carbon (1 g) were added and catalytic reduction was applied for 4 hours. After removing catalyst by filtration, the solvent was dissolved off and the residue was dissolved in DMF (50 ml). An azide ingredient prepared from Z-Tyr(Bzl)-D.Ala-Gly-NHNH$_2$ (1.30 g, 2.38 mmol) and triethylamine (0.70 ml, 2.38 mmol) were added and stirred at 4° C. for 24 hours. After distilling off DMF, water was added to the residue to obtain powder. The powder was collected by filtration and washed with an aqueous 10% solution of citric acid, an aqueous 5% solution of sodium hydrogen carbonate, an aqueous saturated solution of sodium chloride and water successively. After drying, it was recrystallized from methanol - isopropyl ether.

Yield: 1.39 g (81%), Melting point: 145°–149° C.

Rf$_1$: 0.75

Elemental analysis C$_{54}$H$_{66}$N$_6$O$_8$·½H$_2$O Calculated value: C 69.28, H 7.28, N 8.98 Measured value: C 69.25, H 7.14, N 8.85

(4) Preparation of H-Tyr-D.Ala-Gly-Phe-Leu-NHAda.

Z-Tyr(Bzl)-D.Ala-Gly-Phe-Leu-NHAda (500 mg, 0.54 mmol) was dissolved in THF (30 ml), to which two drops of acetic acid and 5% palladium-carbon (1 g) were added and catalytic reduction was applied for 4 hours. After removing the catalyst by filtration, the solvent was distilled off and the residue was dissolved in a small amount of chloroform. A fraction showing a single spot was obtained by silica gel column chromatography using chloroform - methanol (10:1) as an eluting solution. After distilling off the solvent, ether was added to the residue to obtain powder.

Yield: 155 mg (41%), Melting point: 141°–145° C.

Rf$_1$: 0.51, [α]$_D$=+32.5° (C=0.2, DMF, 25° C.)

Elemental analysis C$_{39}$H$_{54}$N$_6$O$_9$·2H$_2$O Calculated value: C 63.39, H 7.91, N 11.37 Measured value: C 63.76, H 7.85, N 11.21

FAB-MS: 703.0 [M+H]$^+$

Amino acid analysis value after hydrolysis with 6N hydrogen chloride

Gly 1.04, Ala 1.03, Leu 1.00, Tyr 1.00, Phe 1.07

Example 3

Preparation of H-Tyr-D.Ala-Gly-Phe-Leu-O-CH$_2$-Ada and H-Tyr-D.Ala-Gly-Phe-Leu-O-(CH$_2$)$_2$-Ada (1) Preparation of Z-Leu-O-CH$_2$-Ada Z-Leu-OH (2.10 g, 7.9 mmol) was dissolved in methylene chloride (30 ml), to which 1-adamantane methanol (1.31 g, 7.9 mmol), DCC (1.8 g, 8.7 mmol) and DMAP (97 mg, 0.79 mmol) were added and stirred at 4° C. for 48 hours. After removing the resultant urea derivative by filtration, the solvent was distilled off. The residue was dissolved in ethyl acetate, and ethyl acetate layer was washed with an aqueous 5% solution of sodium carbonate, an aqueous 10% solution of citric acid, an aqueous saturated solution of sodium chloride and water successively. After drying with sodium sulfate, ethyl acetate was distilled off. Further, the residue was dissolved in chloroform and purified by silica gel column chromatography to obtain an oily product showing a single spot.

Yield: 2.43 g (74%)

Rf$_3$: 0.88

FAB-MS: 414.2 [M+H]$^+$ (1') Preparation of Z-Leu-O-CH$_2$-CH$_2$-Ada

The procedures were the same as those in (1) above except for using 1-adamantane ethanol (1.70 g, 9.4 mmol) instead of 1-adamantane methanol.

Yield: 1.85 g (46%)

Rf$_5$: 0.63

FAB-MS: 428.0 [M+H]$^+$ (2) Preparation of Z-Phe-Leu-O-CH$_2$-Ada

Z-Leu-O-CH$_2$-Ada (2.18 g, 5.27 mmol) was dissolved in THF (20 ml), to which 5% palladium-carbon (about 2 g), acetic acid (2 ml) were added and catalytic reduction was applied for 10 hours. After removing the palladium-carbon by filtration, the filtrate was concentrated and the residue was dissolved in DMF (20 ml). Triethylamine (0.74 ml, 5.27 mmol) and Z-Phe-ONP (2.21 g, 5.27 mmol) and N-hydroxybenzotriazole (0.36 g, 2.64 mmol) were added and stirred for 24 hours. After distilling off DMF, the residue was dissolved in ethyl acetate and washed with an aqueous 5% solution of sodium carbonate, an aqueous 10% solution of citric acid, an aqueous saturated solution of sodium chloride and water successively. After drying with sodium sulfate, ethyl acetate was distilled off. Further, the residue was dissolved in chloroform and purified by silica gel column chromatograph using chloroform - methanol (20:1) as an eluting solution to obtain an oily product showing a single spot.

Yield: 2.19 g (99%)

Rf$_4$: 0.46

FAB-MS: 561.3 [M+H]$^+$ (2') Preparation of Z-Phe-Leu-O-(CH$_2$)$_2$-Ada

The procedures were the same as those in (2) above except for using Z-Leu-O-CH$_2$-CH$_2$-Ada (1.85 g, 4.33 mmol) instead of Z-Leu-O-CH$_2$-Ada.

Yield: 2.49 g (100%)

Rf$_5$: 0.15

FAB-MS: 575.0 [M+H]$^+$ (3) Preparation of Z-Tyr(Bzl)-D-Ala-Gly-Phe-Leu-O-CH$_2$-Ada Z-Phe-Leu-O-CH$_2$-Ada (2.0 g, 3.57 mmol) was dissolved in tetrahydrofuran (15 ml), to which 5% palladium-carbon (about 2 g) and acetic acid (1 ml) were added and catalytic reduction was applied for 5 hours. After removing the catalyst by filtration, the filtrate was concentrated. The residue was dissolved in DMF (10 ml), to which an azide ingredient prepared from Z-Tyr(Bzl)-D.Ala-Gly-NHNH$_2$ (1.60 g, 2.92 mmol) and triethylamine (0.27 ml, 1.95 mmol) were added and stirred at 4° C. for 48 hours. After distilling off DMF, the residue was dissolved in ethyl acetate and washed with aqueous 5% solution of sodium carbonate, an aqueous 10% solution of citric acid, an aqueous saturated solution of sodium chloride and water successively. After drying with sodium sulfate, ethyl acetate was distilled off under a reduced pressure and ether was added to the residue to obtain powder. Further, it was dissolved in chloroform and purified by silica gel column chromatography using chloroform - methanol (20:1) as an eluting solution, to obtain a product showing a single spot, which was recrystallized from methanol ether.

Yield: 0.70 g (38%), Melting point: 158°–162° C.

Rf$_3$: 0.34 [α]$_D$=−17.2° (C=0.5, DMF)

Elemental analysis: C$_{55}$H$_{67}$N$_5$O$_9$·½H$_2$O Calculated value: C 69.45, H 7.21, N 7.36 Measured value: C 69.61, H 7.29, N 7.79

(3') Preparation of Z-Tyr(Bzl)-D.Ala-Gly-Phe-Leu-O-(CH$_2$)$_2$-Ada

Z-Phe-Leu-O-(CH$_2$)$_2$-Ada (1.15 g, 2 mmol) was dissolved in tetrahydrofuran (15 ml), to which 5% palladium-carbon (about 2 g) and 5 ml of acetic acid were added and catalytic reduction was applied for 5 hours. After removing the catalyst by filtration, the filtrate was concentrated. The residue was dissolved in DMF (10 ml), to which an azide ingredient prepared from Z-Tyr(Bzl)-D.Ala-Gly-NHNH$_2$ (1.2 g, 2.19 mmol) and triethylamine (0.28 ml, 2 mmol) were added and stirred at 4° C. for 48 hours. After distilling off DMF, the residue was dissolved in ethyl acetate and washed with aqueous 5% solution of sodium carbonate, an aqueous 10% solution of citric acid, an aqueous saturated solution of sodium chloride and water successively. After drying with sodium sulfate, ethyl acetate was distilled off under a reduced pressure and ether was added to the residue, to obtain powder. Further, it was dissolved in chloroform and purified by silica gel column chromatography using chloroform - methanol (30:1) as an eluting solution, to obtain a product showing a single spot, which was recrystallized from methanol ether.

Yield: 0.84 g (51%), Melting point: 148°–151° C.

Rf$_3$: 0.31, $[\alpha]_D$=−13.3° (C=0.6, DMF)

Elemental analysis: $C_{56}H_{69}N_5O_9 \cdot 1.5H_2O$ Calculated value: C 68.41, H 7.38, N 7.12 Measured value: C 68.44, H 7.09, N 7.46

(4) Preparation of H-Try-D.Ala-Gly-Phe-Leu-O-CH$_2$-Ada

Z-Tyr(Bzl)-D.Ala-Gly-Phe-Leu-O-CH$_2$-Ada (283 mg, 0.3 mmol) was dissolved in acetic acid (10 ml), to which 5% palladium-carbon (1 g) were added and catalytic reduction was conducted for 5 hours. After removing the catalyst by filtration, the filtrate was diluted with water and then freeze-dried. The freeze drying product was dissolved in 5% acetic acid, placed in a Diaion HP-20 column and washed with 5% acetic acid (200 ml). Then, it was eluted with gradient elution using 5% acetic acid (200 ml) and acetonitrile (200 ml) and the main fraction was concentrated and freeze-dried, to obtain white feather like crystals.

Yield: 135 mg (56%)

Rf$_1$: 0.30 $[\alpha]_D$=+6.3° (C=0.2, DMF)

FAB-MS: 718.0 [M+H]$^+$

Elemental analysis: $C_{41}H_{54}N_5O_7 \cdot 1.5H_2O$ Calculated value: C 65.14, H 7.60, N 9.27 Measured value: C 65.15, H 7.61, N 9.39

(4') Preparation of H-Tyr-D.Ala-Gly-Phe-Leu-O-(CH$_2$)$_2$-Ada

Z-Tyr-(Bzl)-D.Ala-Gly-Phe-Leu-O-(CH$_2$)$_2$-Ada (287 mg, 0.3 mmol) was dissolved in 10 ml of acetic acid, to which 1 g of 5% palladium-carbon was added and catalytic reduction was applied for 5 hours. After removing the catalyst by filtration, the filtrate was diluted with water and then freeze-dried. The freeze drying product was dissolved in 5% acetic acid, placed on a Diaion HP-20 column and washed with 5% acetic acid (200 ml). Then, it was eluted by gradient elution using 5% acetic acid (200 ml) and acetonitrile (200 ml). The main fraction was concentrated and freeze-dried to obtain white feather-like crystals.

Yield: 110 mg (50%), Melting point: 117°–122° C.

Rf$_1$: 0.28 $[\alpha]_D$ =+34.9° (C=0.2, DMF)

FAB-MS: 732.0 [M+H]$^+$

Elemental analysis: $C_{41}H_{57}N_5O_7 \cdot 1.5H_2O$ Calculated value: C 64.88, H 7.97, N 9.23 Measured value: C 64.61, H 7.72, N 8.91

Example 4

Adamantylated enkephalin derivatives a and b obtained in Examples 1 and 2 were examined for in vivo analgesic effect and in vitro suppressing effect to shrinkage of extirpated intestine of guinea pig by electric stimulations.

Measurement for in Vivo Analgesic Activity

Figure 2:
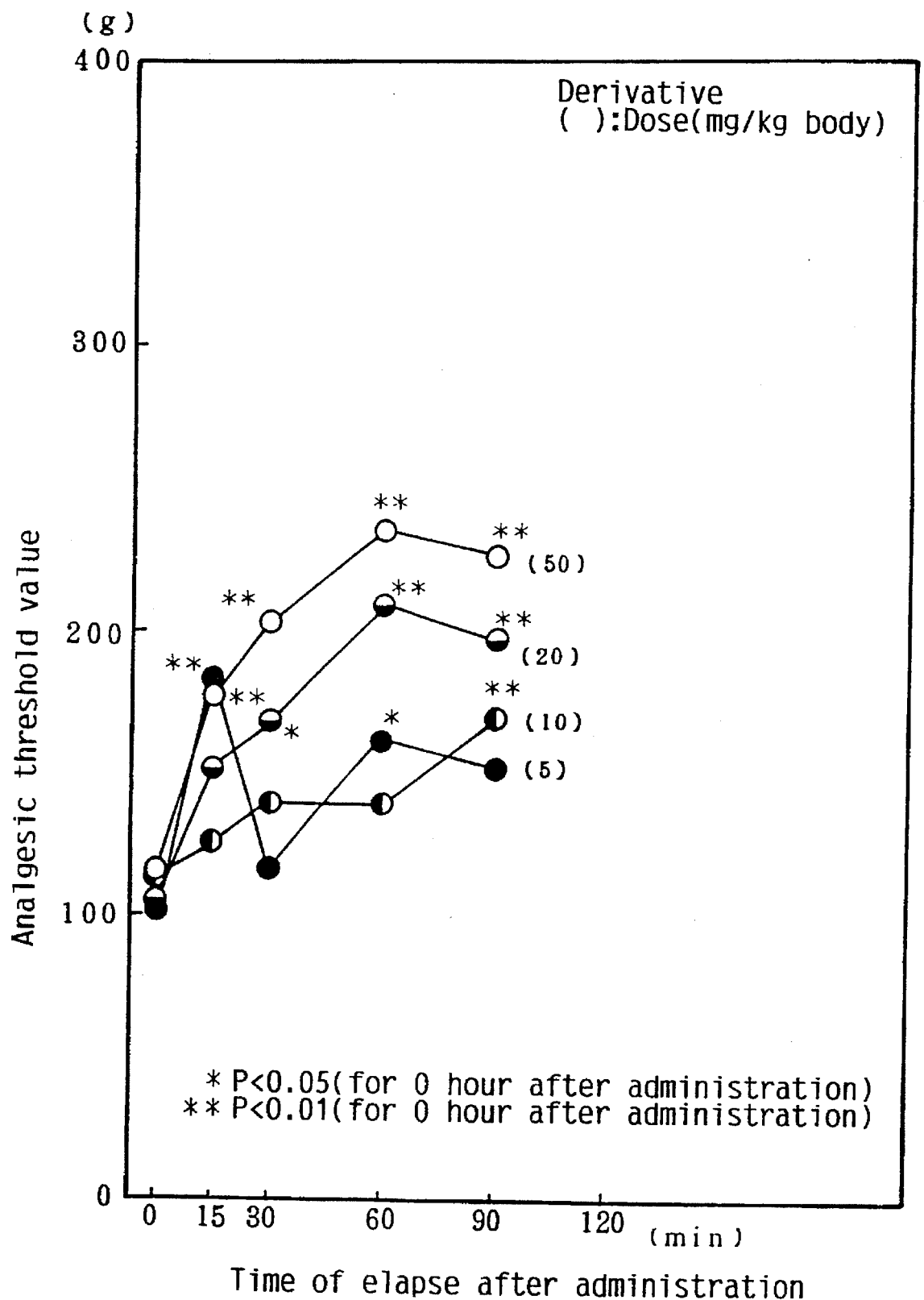
Figure 3:
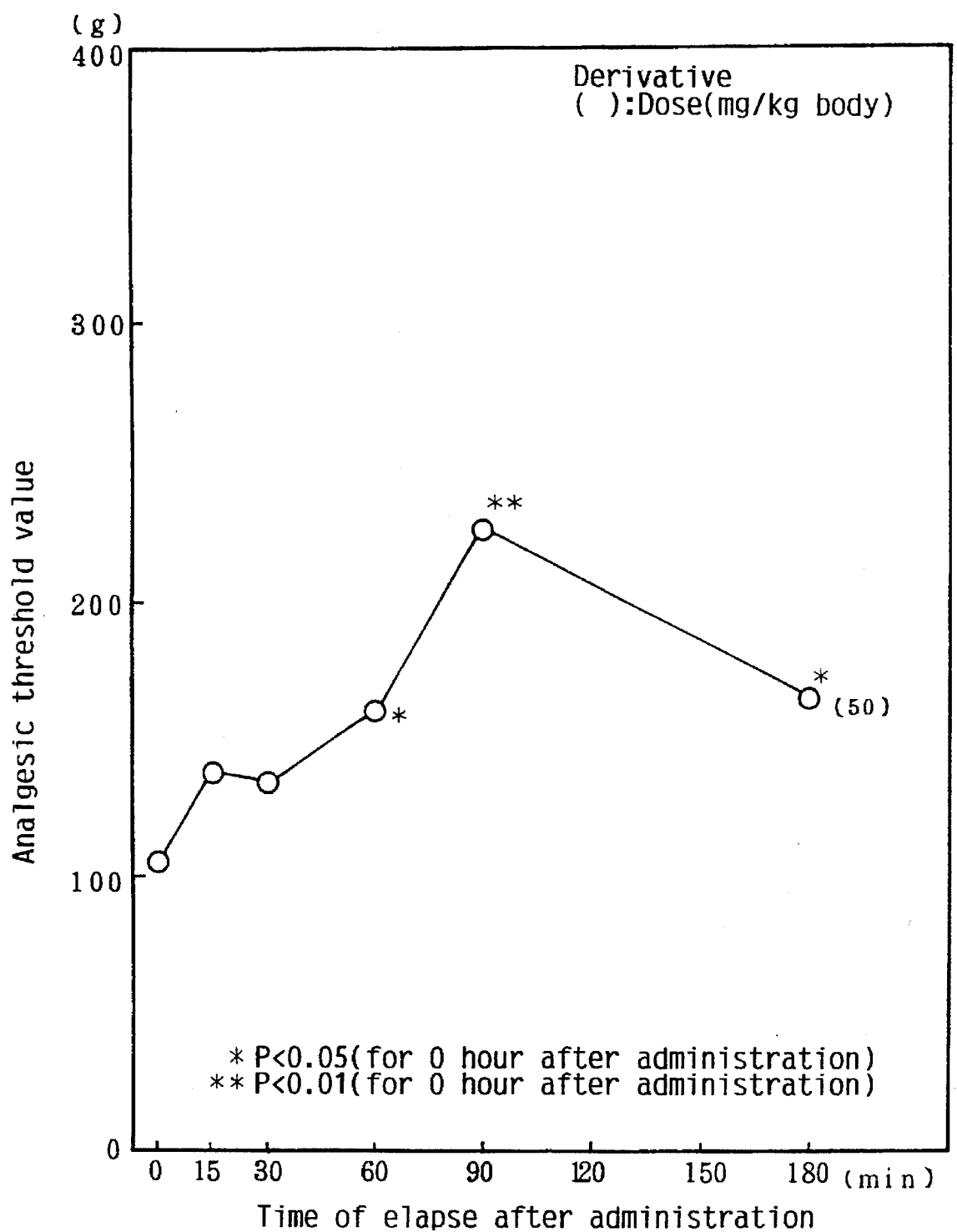
FIG. 3 is a graph illustrating the result of measurement for the in vivo analgesic activity of the derivative b.
Figure 4:
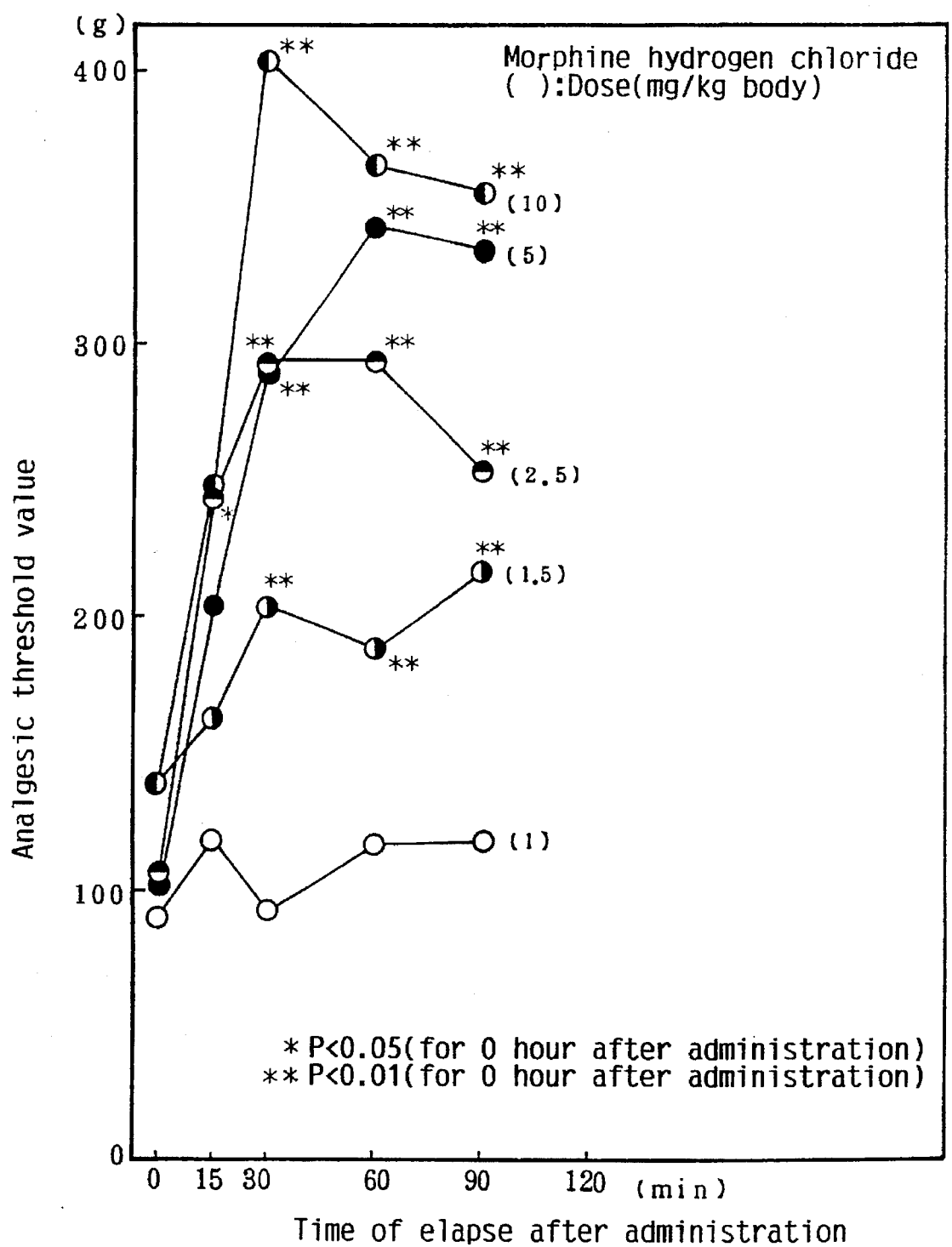
FIG. 4 is a graph illustrating the result of measurement for in vivo analgesic activity of morphine hydrogen chloride.
Figure 5:
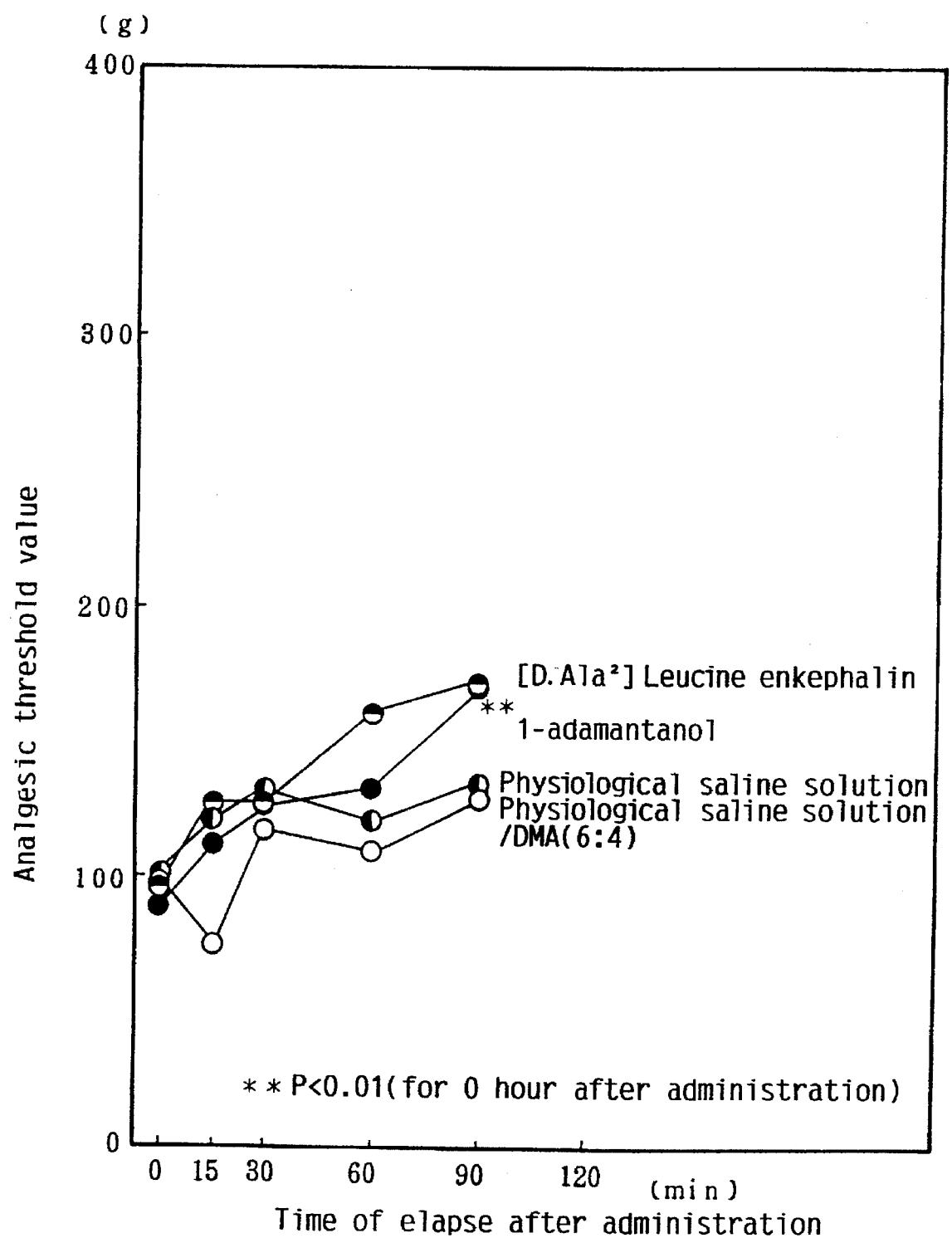
FIG. 5 is a graph illustrating the result of measurement for in vivo analgesic activity of the control.

Adamantylated enkephalin derivatives a and b are subcutaneously administrated to a mouse, and an analgesic effect in the central nervous system was measured by Randall Selitto method. That is, the derivatives a and b were dissolved in a mixed solution of DMA: physiological saline solution (4:6) and about 100 µl of the solution was subcutaneously administrated to a mouse (dd-Y series: about 20 g) (1–50 mg/kg), and the analgesic effect was measured on every predetermined time interval after the administration by the Randall Selitto method. Morphine hydrogen chloride was used as a comparative drug and [D-Ala$^2$] leucine enkephalin, 1-adamantanol, physiological saline solution and mixed solvent of physiological saline solution+DMA (6:4) were used as controls, respectively. The test results are shown in FIG. 2 (derivative a), FIG. 3 (derivative b), FIG. 4 (morphine hydrogen chloride) and FIG. 5 (control).

The derivatives a and b having adamantyl group introduced on the C-terminus showed analgesic activity inferior to morphine hydrogen chloride but superior to the controls.

Measurement for in Vitro Analgesic Activity

A suppressing effect for the shrinkage of extirpated intestine of guinea pig of the adamantylated enkephalin derivatives a and b was measured in accordance with the method of Kosterlitz (H. W. Kosterlitz, A. A. Watterfield, Ann. Rev. Pharmacol., 15, 29, (1975)). Further, morphine hydrogen chloride was used as a comparative drug and [D-Ala$^2$] leucine enkephalin was used as a control. The test results are shown in Table 1.

TABLE 1

| Compound | ED$_{50}$ (mol) (mean ± s.e.m.) | Relative Potency |
|---|---|---|
| Morphine hydrogen chloride | $3.2 \pm 0.43 \times 10^{-8}$ (n = 17) | 1.00 |
| [D-Ala$^2$] Leucine enkephalin | $3.6 \pm 1.17 \times 10^{-8}$ (n = 7) | 0.89 |
| Derivative a | $9.4 \pm 4.82 \times 10^{-8}$ (n = 7) | 0.34 |
| Derivative b | $1.5 \pm 0.71 \times 10^{-8}$ (n = 5) | 2.13 |

Each of the derivatives a and b showed suppression for shrinkage each of which was antagonized by naloxon. That is, it can be seen that the derivatives have morphine-like activity irrespective of introduction of the adamantyl group.

From the test results described above, it can be confirmed that the adamantylated enkephalins show morphine-like analgesic effect by hypodermic administration. This shows improvement in the BBB permeability and clinical application as a hypodermic injection solution is expected if the safety is confirmed.

From the results described above, it is shown that the BBB permeability is improved by the introduction of the adamantyl group while keeping the physiological activity and similar effects can also be expected to analogous derivatives. However, since it may be considered that the activity is lost depending on the position of introducing the adamantyl group in view of the nature of the physiological active substance, a sufficient care is necessary upon introduction.

Further, introduction of the adamantyl group by the following reaction was attempted to zidovudine (azide thymidine, hereinafter simply referred to as AZT) as an anti-vital chemical therapeutical agent.

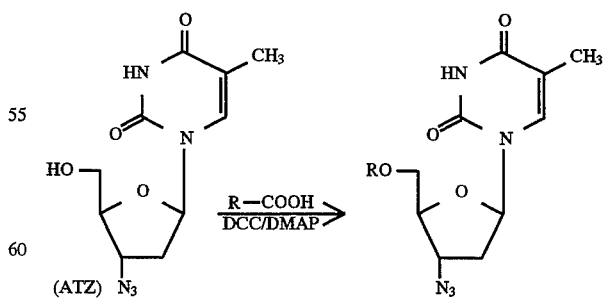

R used herein represents:

(1) -CO-Ada derivative e (2) -CO-CH$_2$-Ada derivative f (3) -Gly-CO-Ada derivative g (4) -β.Ala-CO-Ada derivative h
(5) -GABA-CO-Ada derivative i Description will now be made more specifically.

Example 5

Preparation of AZT-CO-Ada (derivative e)

Ada-COOH (135 mg, 0.8 mmol) were dissolved in DMF (10 ml), to which AZT (100 mg, 0.37 mmol), DCC (162 mg, 0.79 mmol) and 4,4-dimentylaminopyridine (69 mg, 0.56 mmol) were added under ice cooling and then stirred at 4° C. for 48 hours. After filtering the resultant urea derivative, DMF was distilled off under a reduced pressure and residue was dissolved with addition of ethyl acetate and then washed with 5% solution of sodium hydrogen carbonate, an aqueous saturated solution of sodium chloride and water successively three times for each. After drying the ethyl acetate layer with sodium sulfate, the solvent was distilled off under a reduced pressure, the residue was dissolved in n-hexane - ethyl acetate (7:3) (1 ml), and purified in silica gel column chromatography using the same solvent system as an eluting solution. Fractions containing the aimed product were collected and, after distilling off the solvent under a reduced pressure, the residue was powderized with ether, collected by filtration and then dried.

Yield: 66 mg (41%), Melting point: 120°–123° C.

FT-IR: 2121 cm$^{-1}$ (-N$_3$)

FAB-MS: 430.2 [M+H]$^+$, 452.2 [M+Na]$^+$

Elemental analysis: $C_{21}H_{27}N_5O_5$ Calculated value: C 58.73, H 6.34, N 16.31 Analyzed value: C 59.12, H 6.63, N 16.04

Example 6

Preparation of AZT-CO-CH$_2$-Ada (derivative f)

The procedures were the same as those in Example 6 except for using Ada-CH$_2$COOH instead of Ada-COOH.

Yield: 79.4 mg (48%), Melting point: 95°–99° C.

FT-IR: 2106 cm$^{-1}$ (-N$_3$)

FAB-MS: 444.2 [M+H]$^+$, 466.2 [M+Na]$^+$

Elemental analysis: $C_{22}H_{29}N_5O_5$ Calculated value: C 59.60, H 6.59, N 15.79 Analyzed value: C 59.74, H 6.95, N 15.31

Example 7

(1) Preparation of Ada-CO-NH-CH$_2$-COOH

Glycine (0.98 g, 13 mmol) was dissolved in 150 ml of water containing 4N sodium hydroxide (5 ml, 20 mmol), to which a 10 ml THF solution of 1-adamantane carbonyl-chloride (1.35 g, 6.5 mmol) was added for 30 min, and the reaction solution was vigorously stirred under ice cooling for 3 hours. After the reaction was over, pH was adjusted to 7 with 1N hydrochloric acid, THF was distilled off, the residue was dissolved in ethyl acetate, and the organic layer was washed with 1N hydrochloric acid for three times, an aqueous saturated solution of sodium chloride for three times and then water for three times successively. After drying the ethyl acetate layer with sodium sulfate, the solvent was distilled off and the residue was powderized with addition of ether.

Yield: 73%, Melting point: 200°–203° C.

Elemental analysis: $C_{13}H_{19}NO_3$·¼H$_2$O Calculated value: C 64.59, H 8.13, N 5.80 Analyzed value: C 64.64, H 8.15, N 5.74

(2) Preparation of AZT-CO-CH$_2$-NH-CO-Ada (derivative g)

The procedures were the same as those in Example 6 except for using Ada-CO-Gly-OH instead of Ada-COOH, applying silica gel column chromatography as final purification by using chloroform→chloroform methanol (30:1) as an eluting solution and then powderizing with n-hexane.

Yield: 139.1 mg (76%), Melting point: 95°–98° C.

FT-IR: 2109 cm$^{-1}$ (-N$_3$)

FAB-MS: 487.2 [M+H]$^+$, 509.2 [M+Na]$^+$

Elemental analysis: $C_{23}H_{30}N_6O_6$·¼H$_2$O Calculated value: C 56.26, H 6.26, N 17.12 Measured value: C 56.71, H 6.29, N 16.62

Example 8

(1) Preparation of Ada-CO-β.Ala-OH

Procedures were the same as those in Example 7-(1) except for using β-alanine instead of glycine.

Yield: 85%, Melting point: 187°–192° C.

Elemental analysis: $C_{14}H_{21}NO_3$ Calculated value: C 66.90, H 8.42, N 5.57 Measured value: C 66.82, H 8.63, N 5.32

(2) Preparation of AZT-CO-(CH$_2$)$_2$-NH-CO-Ada (derivative h)

Procedures were the same as those in Example 7 except for using Ada-CO-β.Ala-OH instead of Ada-COOH and powderization with ether after chromatography.

Yield: 143.9 mg (77%), Melting point: 92°–95° C.

FT-IR: 2108 cm$^{-1}$ (-N$_3$)

FAB-MS: 510.3 [M+H]$^+$, 523.3 [M+Na]$^+$

Elemental analysis: $C_{24}H_{32}N_6O_6$·¼H$_2$O Calculated value: C 57.07, H 6.49, N 16.64 Measured value: C 57.39, H 6.75, N 16.12

Example 9

(1) Preparation of Ada-CO-GABA-OH

Procedures were the same as those in Example 7-(1) except for using GABA instead of glycine.

Yield: 84%, Melting point: 163°–166° C.

Elemental analysis: $C_{15}H_{23}NO_3$·¼H$_2$O Calculated value: C 66.76, H 8.78, N 5.19 Measured value: C 67.29, H 9.03, N 5.16

(2) Preparation of AZT-CO-(CH$_2$)$_2$-NH-CO-Ada (derivative i)

Procedures were the same as those in Example 7 except for using Ada-CO-GABA-OH instead of Ada-COOH.

Yield: 159.4 mg (83%), Melting point: 95°–97° C.

FT-IR: 2107 cm$^{-1}$ (-N$_3$)

Elemental analysis: $C_{25}H_{34}N_6O_6$·¼H$_2$O Calculated value: C 57.84, H 6.70, N 16.19 Measured value: C 58.59, H 6.99, N 15.43

Introduction of adamantyl group was attempted to 2-pyrrolidone which was expected as an antidementia drug.

Example 10

2-pyrrolidone (850 mg) and DBU (1.53 g) were dissolved in methylene chloride (20 ml), to which a solution of adamantyl-1-carbonyl chloride (1.98 g) dissolved in methylene chloride (5 ml) was dropped under ice cooling and then left at a room temperature over one night and one day. After washing the organic solvent twice with 0.05N hydrochloric acid (40 ml), and twice with water (40 ml) successively, it was dried with sodium sulfate. The solvent was dried to solidness under a reduced pressure, subjected to column fractionation under the following conditions, the main fraction was separated, dissolved in methylene chloride and recrystallized from hexane to obtain white acicular crystals.

Yield: 400 mg (16%), Melting point: 86°–86.5° C.
Rf$_5$: 0.29
Column Fractionation Condition
Column: ø 3 cm×35 cm
Filler: Kieselgel 60 (230–400 mesh ASTM)
Eluting solution: Methylene chloride The compounds (Examples 5–10) synthesized as described above are introduced with adamantyl groups and it is expected that a preferred BBB permeability is provided to obtain a sufficient intraventricular activity.

We claim:

1. A physiologically active substance represented by the general formula:

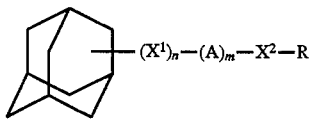

where $X^1$ and $X^2$, which may be identical with or different from each other, represent an ester bond, or amide bond, A represents a lower alkylene group in which n=0 if m=0, n=0 or 1 if m=1, R represents a residue of a physiologically active substance comprising an amino acid, a phenol-substituted aliphatic amine, an amino sugar, a 5'-O-nucleoside or a N-lactam compound.

2. The substance of claim 1 wherein R represents zidovudine or N-2-pyrrolidone.

3. The substance of claim 1 where R represents an amino acid, an amino sugar or a 5'-O-nucleoside.

4. A physiologically active substance represented by the general formula:

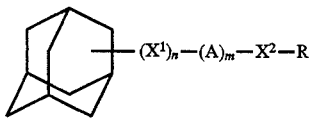

where $X^1$ and $X^2$, which may be identical with or different from each other, represent an ester bond or an amide bond, A represents a lower alkylene group in which n=0 if m=0, n=0 or 1 if m=1, and R represents a pentapeptide, provided that when n=0, m=0, and R is enkephalin, $X^2$ represents an ester bond.

5. The substance of claim 4 which is H-Tyr-D.Ala-Gly-Phe-Leu-O-Ada.

6. A physiologically active substance which is H-Tyr-D.Ala-Gly-Phe-Leu-O-Ada dihydrate.

7. The substance of claim 4 which is H-Tyr-D.Ala-Gly-Phe-Leu-O-CH$_2$-Ada.

8. The substance of claim 4 which is H-Tyr-D.Ala-Gly-Phe-Leu-O-CH$_2$-Ada•1.5H$_2$O.

9. The substance of claim 4 which is H-Tyr-D.Ala-Gly-Phe-Leu-O-(CH$_2$)$_2$-Ada.

10. The substance of claim 4 which is H-Tyr-D.Ala-Gly-Phe-Leu-O-(CH$_2$)$_2$-Ada•1.5H$_2$O.

11. A physiologically active substance which is H-Tyr-D.Ala-Gly-Phe-Leu-NH-Ada dihydrate.

12. The substance of claim 1 in which said 5'-O-nucleoside is zidovudine (AZT).

13. The substance of claim 12 which is AZT-CO-Ada.

14. The substance of claim 12 which is AZT-CO-CH$_2$-Ada.

15. The substance of claim 12 which is AZT-Gly-CO-Ada.

16. The substance of claim 12 which is AZT-β.Ala-CO-Ada.

17. The substance of claim 12 which is AZT-GABA-CO-Ada, wherein GABA is gamma-aminobutyric acid.

18. The substance of claim 1 in which R is N-2-pyrrolidone.

* * * * *